US006183460B1

(12) United States Patent
Smith et al.

(10) Patent No.: US 6,183,460 B1
(45) Date of Patent: Feb. 6, 2001

(54) MULTI-USE SOLUTION CONTAINER HAVING FLAPS

(75) Inventors: Sidney T. Smith, Lake Forest; Joan Zietlow, Winnetka; Keith Anderson, Libertyville, all of IL (US)

(73) Assignee: Baxter International Inc., Deerfield, IL (US)

( * ) Notice: Under 35 U.S.C. 154(b), the term of this patent shall be extended for 0 days.

(21) Appl. No.: 09/010,691

(22) Filed: Jan. 22, 1998

(51) Int. Cl.$^{7}$ .................................................... A61B 19/00

(52) U.S. Cl. .......................... 604/408; 604/410; 209/783

(58) Field of Search .................................... 604/408, 410, 604/411; 383/38, 86.2, 87, 88, 901; 206/438, 778, 783

(56) References Cited

U.S. PATENT DOCUMENTS

| | | | |
|---|---|---|---|
| 2,693,189 | 11/1954 | Ryan . | |
| 2,949,712 * | 8/1960 | Bieberdorf et al. . | |
| 3,042,086 * | 7/1962 | Winchell . | |
| 3,255,923 | 6/1966 | Soto . | |
| 3,545,671 * | 12/1970 | Ross | 604/410 |
| 3,915,212 * | 10/1975 | Bujan et al. | 206/438 |
| 4,085,244 | 4/1978 | Stillman . | |
| 4,112,989 | 9/1978 | Grode et al. . | |
| 4,199,062 | 4/1980 | Johnston et al. . | |
| 4,322,465 | 3/1982 | Webster . | |
| 4,405,667 | 9/1983 | Christensen et al. . | |
| 4,407,888 | 10/1983 | Crofts . | |
| 4,421,235 | 12/1983 | Moriya . | |
| 4,479,989 | 10/1984 | Mahal . | |
| 4,497,857 | 2/1985 | Bonis . | |
| 4,548,348 | 10/1985 | Clements . | |
| 4,636,412 | 1/1987 | Field . | |
| 4,654,240 | 3/1987 | Johnston . | |
| 4,686,125 | 8/1987 | Johnston et al. . | |
| 4,692,361 | 9/1987 | Johnston et al. . | |
| 4,705,708 | 11/1987 | Briggs et al. . | |
| 4,724,961 | 2/1988 | Shimoyamada et al. . | |
| 4,764,404 | 8/1988 | Genske et al. . | |
| 4,767,651 | 8/1988 | Starczewski et al. . | |
| 4,772,497 | 9/1988 | Maasola . | |
| 4,778,697 | 10/1988 | Genske et al. . | |
| 4,803,102 | 2/1989 | Raniere et al. . | |
| 4,885,119 | 12/1989 | Mueller et al. . | |
| 4,910,085 | 3/1990 | Raniere et al. . | |
| 4,910,147 | 3/1990 | Bacehowski et al. . | |
| 4,939,151 | 7/1990 | Bacehowski et al. . | |
| 4,966,795 | 10/1990 | Genske et al. . | |
| 4,978,579 | 12/1990 | Rosenbaum . | |
| 5,017,490 | 5/1991 | Taiariol et al. . | |
| 5,024,536 * | 6/1991 | Hill | 383/38 |
| 5,066,290 | 11/1991 | Measells et al. . | |
| 5,071,686 | 12/1991 | Genske et al. . | |
| 5,093,164 | 3/1992 | Bauer et al. . | |
| 5,098,202 | 3/1992 | Rosenbaum . | |
| 5,108,844 | 4/1992 | Blemberg et al. . | |
| 5,110,642 | 5/1992 | Genske . | |

(List continued on next page.)

FOREIGN PATENT DOCUMENTS

| | | |
|---|---|---|
| 0 092 897 | 2/1983 | (EP) . |
| 0 148 161 | 1/1985 | (EP) . |
| 2 253 496 | 4/1975 | (FR) . |
| 2 591 101 | 12/1987 | (FR) . |
| WO 83/00158 | 4/1982 | (WO) . |
| WO 90/03427 | 9/1989 | (WO) . |
| WO 93/09718 | 11/1992 | (WO) . |

*Primary Examiner*—Mark O. Polutta
*Assistant Examiner*—David J. Cho
(74) *Attorney, Agent, or Firm*—Mark J. Buonaiuto; Joseph A. Fuchs

(57) ABSTRACT

The present invention provides a container for holding medical solutions, wherein the container comprises a fluid-tight chamber, the chamber having opposing first and second edges and opposing first and second surfaces, and a flap extending from an edge of the chamber and being hingedly connected to the chamber.

26 Claims, 8 Drawing Sheets

U.S. PATENT DOCUMENTS

| | | | | |
|---|---|---|---|---|
| 5,129,894 | | 7/1992 | Sommermeyer et al. . | |
| 5,135,785 | | 8/1992 | Millon . | |
| 5,139,831 | | 8/1992 | Mueller . | |
| 5,139,946 | | 8/1992 | Howell et al. . | |
| 5,176,634 | | 1/1993 | Smith et al. . | |
| 5,196,254 | | 3/1993 | Akiyama . | |
| 5,207,509 | * | 5/1993 | Herbert | 383/38 |
| 5,225,346 | | 7/1993 | Matsumiya et al. . | |
| 5,257,985 | * | 11/1993 | Puhl | 604/410 |
| 5,288,531 | | 2/1994 | Falla et al. . | |
| 5,295,964 | * | 3/1994 | Gauthier | 604/408 |
| 5,306,542 | | 4/1994 | Bayer . | |
| 5,310,676 | | 5/1994 | Johansson et al. . | |
| 5,388,699 | * | 2/1995 | Ratajczak et al. | 206/438 |
| 5,520,972 | | 5/1996 | Ezaki et al. . | |
| 5,533,653 | * | 7/1996 | Kaufman | 383/38 |
| 5,560,403 | * | 10/1996 | Balteau et al. | 604/408 |
| 5,820,582 | * | 10/1998 | Keilman | 604/49 |
| 5,824,216 | * | 10/1998 | Joie et al. | 604/408 |

* cited by examiner

MULTI-USE SOLUTION CONTAINER HAVING FLAPS

TECHNICAL FIELD

The present invention relates generally to a container for holding medical solutions, and more specifically to a container for holding medical solutions having one or more flaps hingedly connected and extending from an edge of a fluid-tight chamber.

BACKGROUND OF THE INVENTION

In the medical field, various containers have been used to hold medical solutions such as blood, hemoglobin solutions or other blood substitutes, chemotherapeutic solutions, and other intravenous drip solutions. Frequently, these containers are bags which are either molded or fabricated from flexible plastic so they include one or more expandable chambers for holding medical solution. Additionally, one or more spouts generally extend outward from the chambers for filling and/or draining the container. These spouts are closed to seal the chambers until they are ready to be emptied.

Labels are usually applied to the container for carrying information regarding the medical solution held by the container. For instance, the label may describe the chemical composition of the solution held in the container, it may provide information regarding the origin or use of the medical solution, and/or it may provide regulatory information concerning the medical solution. Various agencies, including regulatory agencies, and jurisdictions generally require certain information to be present on the label in a specific form. For instance, regulatory agencies typically require the information to be provided in one or more specific languages.

Conventional small-volume solution containers have labeling space for only a limited amount of information. As a result of this limitation, a single label fixed to the container and providing all the information required by multiple regulatory agencies cannot be made. Therefore, medical solution manufacturers and distributors must anticipate where solutions will be needed and label the containers appropriately. However, this creates additional inventory problems. Alternatively, the manufacturers and distributors can wait until an order is placed and then label the containers so they include the information in the appropriate form required by the agency or agencies regulating the destination jurisdiction. However, both of these alternatives create problems and add expense to the distribution process.

Further, when the medical solution requires refrigeration prior to labeling, condensate forms on the exterior of the container as it warms. This condensate hampers labeling because adhesives may not stick to the wetted container. In addition, inks may run and become illegible if they come in contact with the condensate.

An additional problem includes the use of overpouches in conjunction with the medical container. When packaging the medical solution containers for shipment, the containers are generally placed in an overpouch. An overpouch is used to protect the medical container during shipment and storage. The overpouch usually takes the form of a bag which can be sealed following insertion of the medical solution container. However, protecting medical containers with overpouches is expensive and inefficient.

When using an overpouch, the medical container must be physically placed into an additional element. Thus, the manufacturer must not only manufacture the medical container itself, but must also manufacture or stock the overpouch. This increases cost and assembly time. Additionally, the overpouch itself is not often made of a material which can be easily seen through for visual inspection of the medical container itself, the information on the label of the medical container or the contents of the medical container. It is very important that the contents of the medical solution be visible to those who work with the medical containers such that a quick and detailed inspection of the solution for particulate matter, precipitates, or other visualizable contaminants, along with the information on the labeling of the container, can be performed. Thus, the use of a separate overpouch has several drawbacks.

SUMMARY OF THE INVENTION

The present invention provides a container for holding medical solutions. The container comprises a fluid-tight chamber having opposing first and second edges and opposing first and second surfaces. At least one flap extends from an edge of the chamber and is hingedly connected to the chamber. The flaps have multiple uses: they can carry information regarding the medical solution within the container; they can be utilized as a protective covering for the container; and, they can be utilized in combination as information carriers and protective coverings.

In general, a first flap extends from a first edge of the chamber and a second flap extends from a second edge of the chamber. The flaps are then generally positioned overlying either the first or second surface of the chamber, depending on the configuration desired.

In one embodiment of the present invention the flaps are utilized as a protective covering. The first flap is positioned such that at least part of the first flap overlies the first surface of the chamber, and the second flap is positioned such that at least part of the second flap overlies the second surface of the chamber. Then, the first and second flaps are sealably connected to form an integrated overpouch. Several variations of the present invention may be noted, including: the provision wherein a single flap is utilized for the entire overpouch element, the provision wherein multiple flaps extend from opposing or adjacent edges of the chamber, and the provision wherein multiple flaps extend from the same edge of the chamber.

In another embodiment of the present invention, the flaps carry information regarding the medical solution held by the container. Providing flaps on a container which carry information increases the labeling area without having to increase the interior volume or the interior surface area. Further, the flaps may include pockets. Information regarding the medical solution held by the container is inserted into the pockets in the flaps. It is also possible to provide flaps carrying information in addition to the flaps that form the overpouch. Preferably, the medical solution container contains multiple flaps wherein the same container has integral information carrier flaps and protective covering flaps.

Briefly, another aspect of the present invention includes a method of making a bag having a chamber capable of defining a fluid-tight volume for holding medical solution and at least one flap. The flap is moveable with respect to the chamber between a deployed position in which the flap extends outward from the chamber, and a stowed position in which the flap at least partially overlies the chamber. The method comprises the steps of superimposing first and second weldable-flexible plastic materials, and welding the first and second materials together along lines forming side, top and bottom seals to form the chamber. The lines are so located as to provide an area extending outwardly from one of the seals thereby forming the flap. The flap is hinged to the chamber at the one seal so as to be swingable between the stowed and deployed positions.

Other features and advantages of the invention will be apparent from the following specification taken in conjunction with the following drawings.

DETAILED DESCRIPTION OF THE PREFERRED EMBODIMENT

Figure 1:
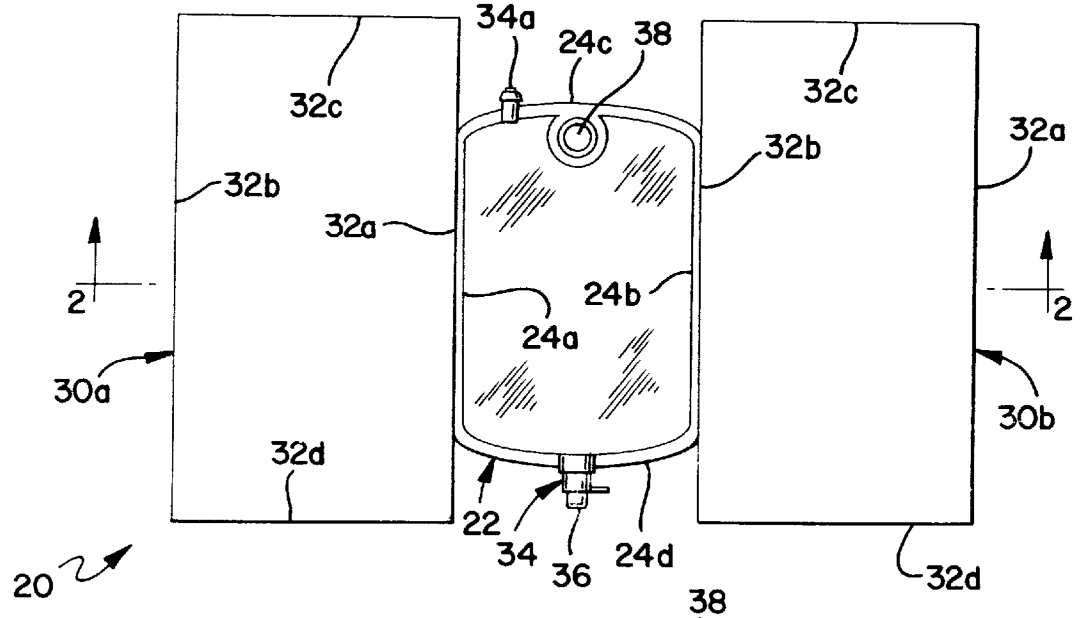
FIG. 1 is a front elevation view of a container of the present invention having a flap utilized as a protective covering.

While this invention is susceptible of embodiments in many different forms, there is shown in the drawings and will herein be described in detail, preferred embodiments of the invention with the understanding that the present disclosure is to be considered as an exemplification of the principles of the invention and is not intended to limit the broad aspect of the invention to the embodiments illustrated.

Figure 2:
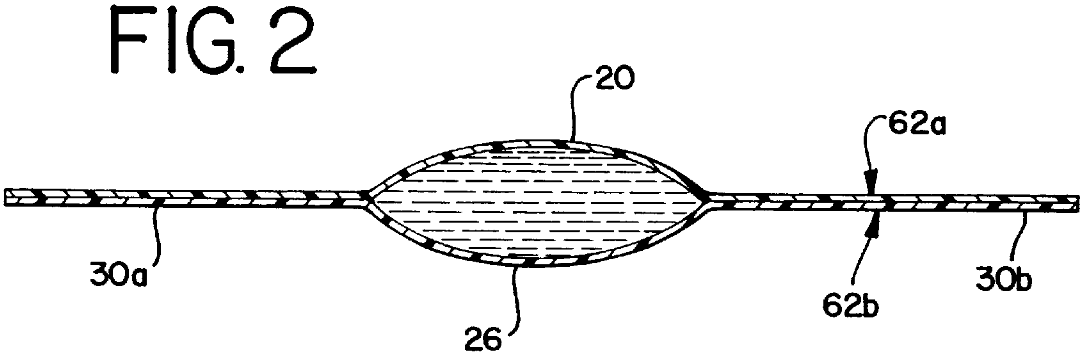
FIG. 2 is a cross section of the container of FIG. 1, taken along line 2—2 of FIG. 1.

Referring now in detail to the drawings and initially to FIG. 1, there is shown a container for medical solutions constructed in accordance with the present invention and designated in its entirety by reference numeral 20. The container comprises a substantially fluid-tight solution chamber (generally indicated at 22) having opposing first and second edges 24*a*,24*b* and opposing first and second surfaces 26,28 as illustrated in FIG. 2. At least one flap, shown in FIG. 1 as first and second flaps 30*a*,30*b*, extends outward from the edges 24*a*,24*b*, of the chamber. The flaps 30*a*,30*b* each have peripheries 32*a*,32*b*,32*c*,32*d*.

Figure 3:
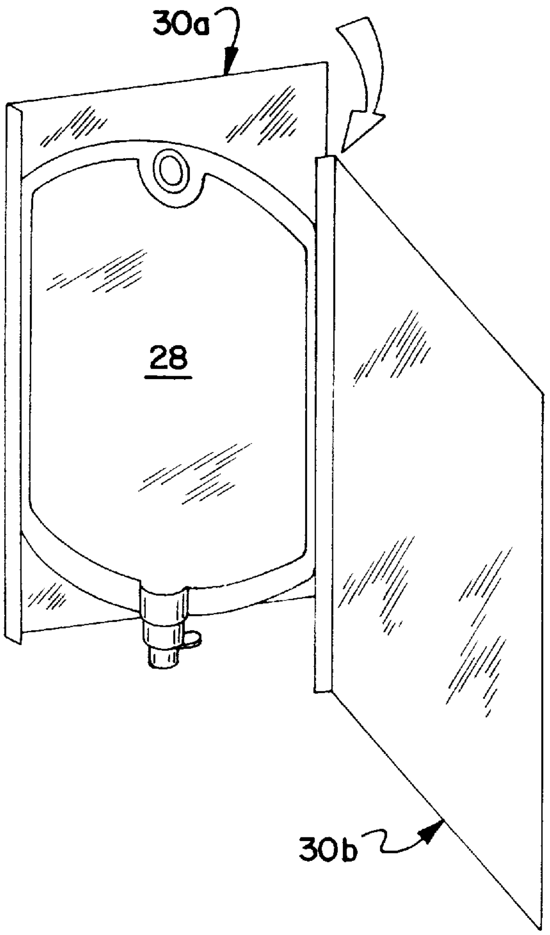
FIG. 3 is a perspective view of the container of FIG. 1 shown with the flaps rotated in a partially deployed, partially stowed position.

Referring back to FIG. 1, the flaps 30*a*,30*b* are hingedly connected to the chamber 22 at an edge 24*a*,24*b* of the chamber 22. The flaps 30*a*,30*b* initially extend away from the chamber 22 in an unfolded or deployed position. Additionally, because of the hinged connection, the flaps 30*a*,30*b* can rotate with respect to the chamber 22, as shown in FIG. 3. To be in a stowed or closed position (see FIG. 4), the flaps 30*a*,30*b* rotate so that at least part of the flaps 30*a*,30*b* overlies a surface 26,28 of the chamber 22. When the flaps overlie a surface of the chamber, the flaps can be utilized as integral protective coverings, illustrated in FIGS. 1, 3 and 4 as flaps 30*a*,30*b*, and/or as information carriers, illustrated in FIGS. 1A and 1B as flaps 130*a*,130*b*.

With further reference to FIG. 1, the container 20 includes a sealable port 34 capable of fluid communication with the interior volume of the solution chamber 22 for filling and draining the interior volume of the solution chamber 22. Further, in the preferred embodiment the container has two ports 34 and 34*a*. One port 34 is utilized as an exit port for transferring medical solution to the patient, and the other port 34*a* is utilized for filling the chamber 22 or adding additional medical solutions to the chamber 22. The ports 34,34*a* are generally formed as a rigid tube to prevent the ports from collapsing and to permit the ports to be connected to standard tubing (not shown) for delivery of medical solution to a patient. The ports 34,34*a* are closed by a re-sealable membrane (not shown) positioned in the port 34,34*a*. Additionally, each port 34,34*a* may be closed by any conventional means, including thermal, radio frequency or solvent welding.

The container 22 also includes a cap 36 removably covering the ports 34,34*a* to prevent dust from entering the container. Additionally, an aperture 38 is provided in the container 20 for hanging the container 20 on a hook. Generally, solution exits the chamber 22 by force of gravity. Therefore, the aperture 38 for hanging the container 20 is placed on an end opposite the port 34 used for transferring the medical solutions to the patient. As such, the container 20 hangs in an inverted position.

Figure 4:
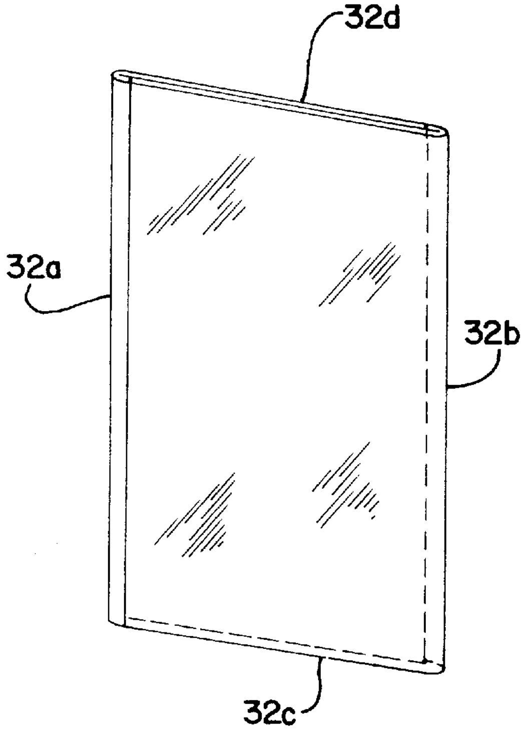
FIG. 4 is a front elevation view of the container of FIG. 1 shown with the flaps in a stowed position.

Referring now to FIGS. 2 and 3, to close the flaps 30*a*,30*b* for sealing, the first flap 30*a* is positioned such that at least part of the first flap 30*a* overlies the first surface 26 of the chamber 22. Similarly, the second flap 30*b* is positioned such that at least part of the second flap 30*b* overlies the second surface 28 of the chamber 22. Then, as shown in FIG. 4, the flaps 30*a*,30*b* are sealably connected proximate their peripheries 32*a*,32*b*,32*c*,32*d* such as to be a protective covering or overpouch for the container 20. Means for sealing the flaps together include, but are not limited to, laser welding, radio frequency welding, thermal welding and solvent welding. Other means for sealing the flaps 30*a*,30*b* together, however, may be utilized. Following the step of sealing the flaps 30*a*,30*b* together, the sealed container 20 is ready to be packaged for shipping or storage until use.

Figure 1A:
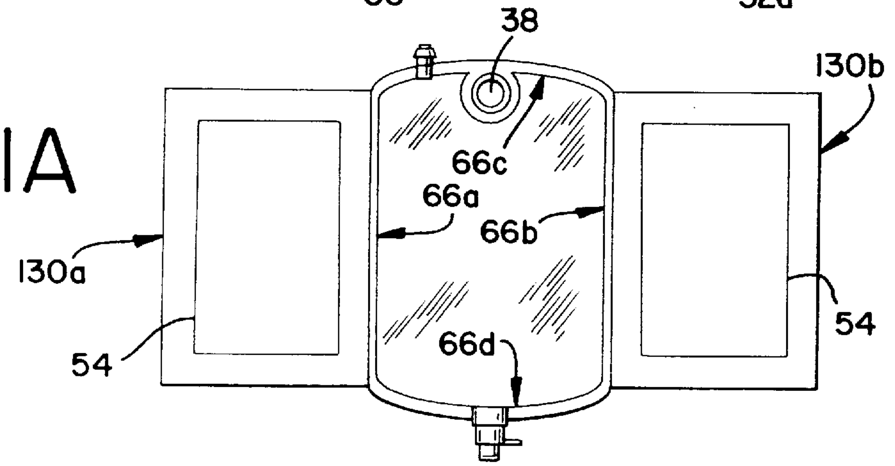
FIG. 1A is a front elevation view of a container of the present invention having a flap utilized as an information carrier.

In another embodiment of the present invention shown in FIG. 1A, the flaps 130*a*,130*b* are utilized to carry information. One means for the flaps 130*a*,130*b* to carry information is through the use of labels 54. Labels 54 containing information regarding the particular medical solution held in the chamber 22 are secured to the flaps 130*a*,130*b* by suitable adhesive means. Alternately, information may be printed or embossed directly on the flaps 130*a*,130*b*.

Figure 1B:
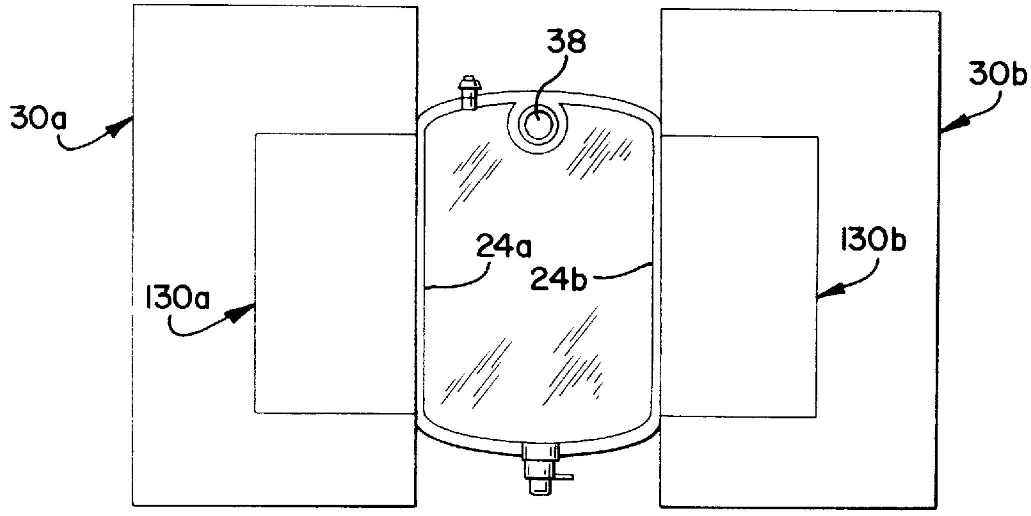
FIG. 1B is a front elevation view of a container of the present invention having flaps utilized as information carriers and as protective coverings.

Another embodiment of the container 20 is shown in FIG. 1B. This embodiment utilizes both protective covering flaps 30*a*,30*b* and information carrying flaps 130*a*,130*b*. A first flap 130*a* for carrying information, and a first flap 30*a* utilized as a protective covering both extend from the first edge 24*a* of the container 20. Additionally, a second flap 130*b* for carrying information, and a second flap 30*b* utilized as a protective covering both extend from the second edge 24*b* of the container 20. In an alternate embodiment (not shown) a single flap could be utilized to both carry information and form a protective covering.

Figure 5:
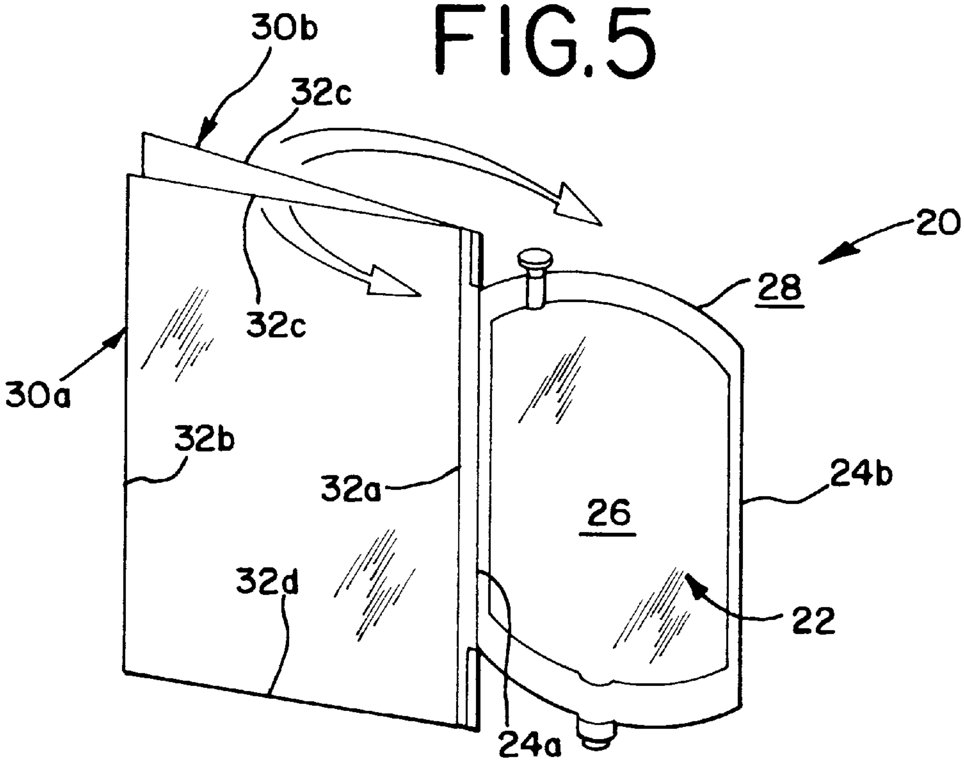
FIG. 5 is a perspective view of a second embodiment of the container of the present invention having multiple flaps extending from the same side of the container.

The embodiment illustrated in FIG. 5 displays a container 20 for medical solutions, wherein a first flap 30*a* is hingedly connected to, and extends outwardly from an edge 24*a* of the solution chamber 22. A second flap 30*b* is also hingedly connected to, and extends outwardly from the same edge 24*a* of the chamber 22. In an unfolded position, each flap 30*a*,30*b* generally initially extends in the same direction away from the solution chamber 22. Upon rotation of the flaps 30*a*,30*b* for closing the container 20, the first flap 30*a* is rotated toward the first side or surface 26 of the chamber 22 and is positioned such that at least part of the first flap 30*a* overlies the first surface 26. Similarly, the second flap 30*b* is rotated toward the second side or surface 28 of the chamber 22 and is positioned such that at least part of the second flap 30*b* overlies the second surface 28. Upon completion of the above steps, the first and second flaps 30*a*,30*b* essentially encapsulate the chamber 22. Finally, flaps 30*a*,30*b* are sealably connected proximate their peripheries 32*a*,32*b*,32*c*, 32*d*.

Figure 5A:
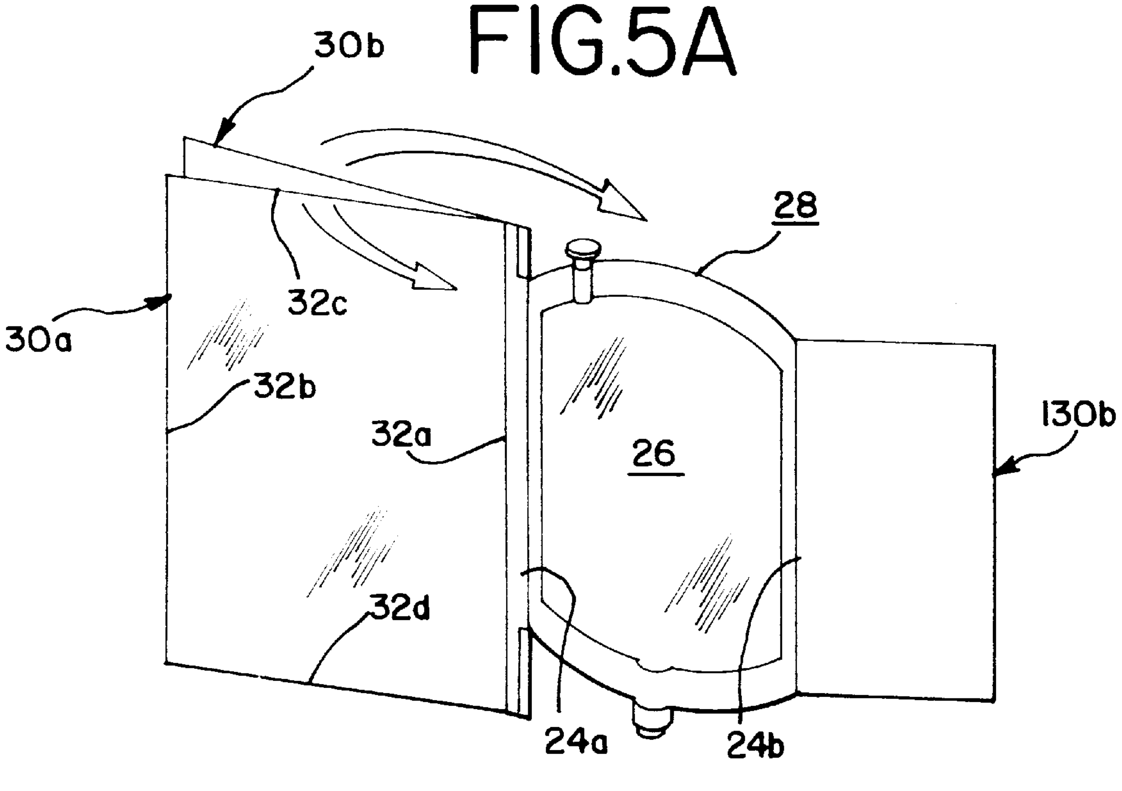
FIG. 5A is a perspective view of a second embodiment of the container of the present invention, and including an information carrier flap extending from the container.

The embodiment illustrated in FIG. 5A is a modification of the embodiment illustrated in FIG. 5. In this embodiment a flap 130*b* for carrying information is hingedly connected to the second edge 24*b* of the chamber 22. As with all embodiments, however, the flap 130*b* can extend from any edge 24*a*,24*b*,24*c*,24*d* of the chamber. Similarly, the flap 130*b* may rotate to at least partially overlie either the first or second surface 26,28.

Figure 6:
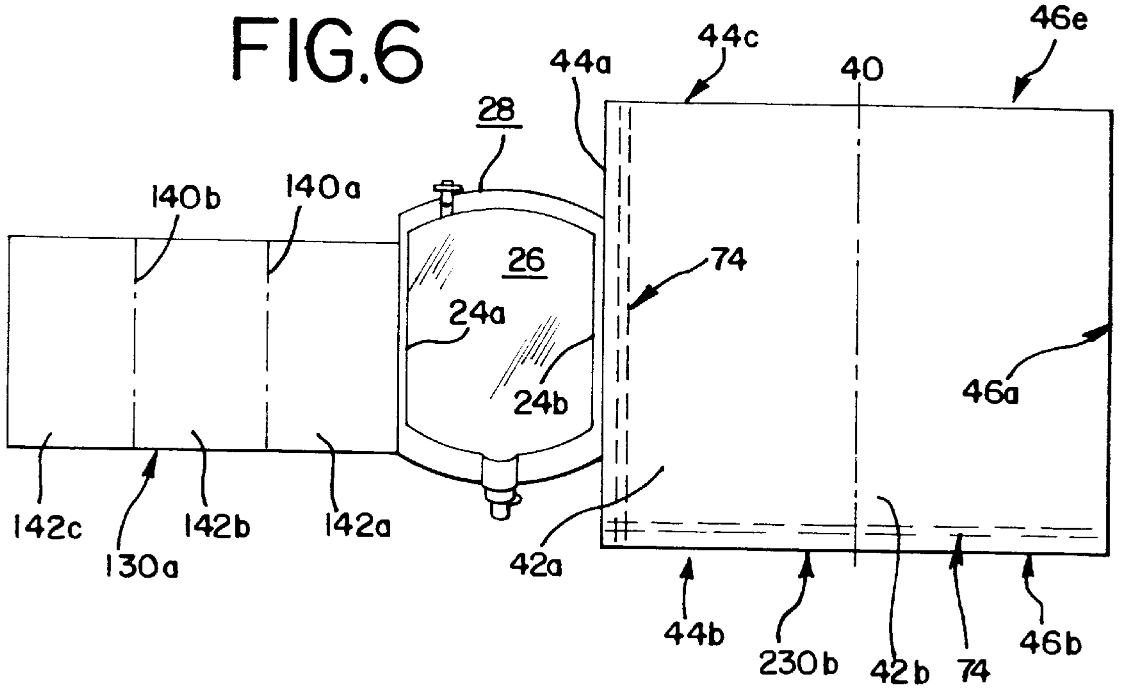
FIG. 6 is a front elevation view of a third embodiment of the container of the present invention having flaps with multiple sections.
Figure 7:
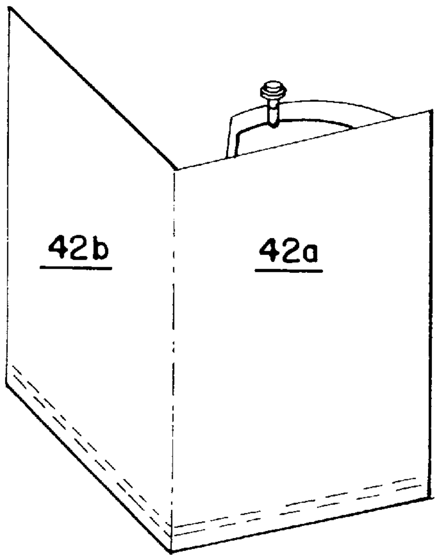
FIG. 7 is a perspective view of the container of FIG. 6 shown with a flap rotated.

The embodiment shown in FIGS. 6 and 7 also comprises a fluid-tight chamber 22. Flap 230*b* is hingedly connected to, and extends from, the second edge 24*b* of the chamber 22. Thus, flap 230*b* can rotate relative to the solution chamber 22. Flap 230*b* in this embodiment, however, is wider than a standard flap, and has a fold-line 40. Fold-line 40 defines first and second sections 42*a*,42*b* of the flap 230*b*. The first section 42*a* has peripheries 44*a*,44*b*,44*c* and the second section 42*b* has peripheries 46*a*,46*b*,46*c*. To position the flap 230*b* in the closed position, the first section 42*a* is rotated and positioned such that at least part of the first section 42*a* overlies the first surface 26 of the chamber 22. Next, the second section 42*b* is rotated about the fold line 40, toward the second surface 28 of the chamber 22, and positioned such that at least part of the second section 42*b* overlies the second surface 28 of the chamber 22. Following the above step, the first and second sections 42*a*,42*b* are positioned on opposite sides or surfaces 26,28 of the chamber 22 and essentially encapsulate the chamber 22. Finally, sections 42*a*,42*b* are sealably connected about their peripheries to create the sealed overpouch around the chamber 22.

The flap 230*b* shown in FIG. 6 also includes a zip strip or sealable strip 74. Each zip strip 74 has male and female elements (not shown). When two zip strips 74 are brought in contact with one another, the male and female components cooperate to form a disengageable seal. The zip strip 74 extends proximate at least one of the peripheries 44*a*,44*b*, of the flap 230*b*. The zip strip 74 removably attaches flaps, or multiple sections of a single flap, together to allow for opening and resealing of the overpouch. The zip strip 74 may be used instead of, or in conjunction with, weldably sealing the overpouch.

The embodiment illustrated in FIG. 6 further displays a flap 130*a* utilized for carrying information. Flap 130*a* is divided by multiple fold-lines 140*a*,140*b* to create multiple sections 142*a*,142*b*,142*c*. Each section provides additional surface area for labeling, including having labeling in different languages in each section. The multiple fold-lines 140*a*,140*b* allow the flap 130*a* to be accordion-folded to the stowed or closed position. In the stowed position, the flap 130*a* at least partially overlies either the first or second surface 26,28 of the container 22.

Figure 8:
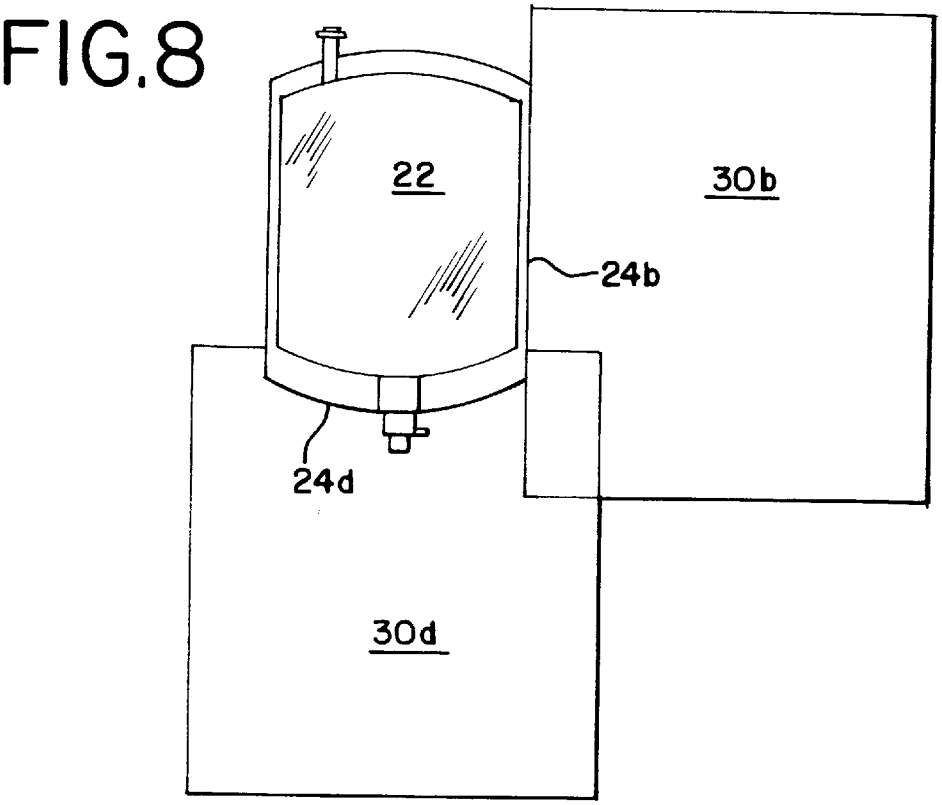
FIG. 8 is a front elevation view of a fourth embodiment of the container of the present invention having flaps extending from adjacent sides of the container.

With reference to FIG. 8, an additional embodiment of the present invention is illustrated. This embodiment comprises at least two flaps 30*b*,30*d* hingedly connected to the chamber 22. The flaps 30*b*,30*d*, however, are hingedly connected to adjacent edges 24*b*,24*d* of the chamber 22, rather than to opposing edges of the chamber 22. Because the flaps 30*b*, 30*d* are hingedly connected to the chamber 22, they can rotate relative to the chamber 22, allowing the flap 30 to at least partially overlie a surface 26,28 of the chamber 22. In general, the first flap 30*b* is positioned such that at least part of the first flap 30*b* overlies the first surface 26. Then, the second flap 30*d* is positioned such that at least part of the second flap 30*d* overlies the second surface 28. The two flaps 30*b*,30*d* are then sealed proximate their peripheries to form the protective covering.

Figure 8A:
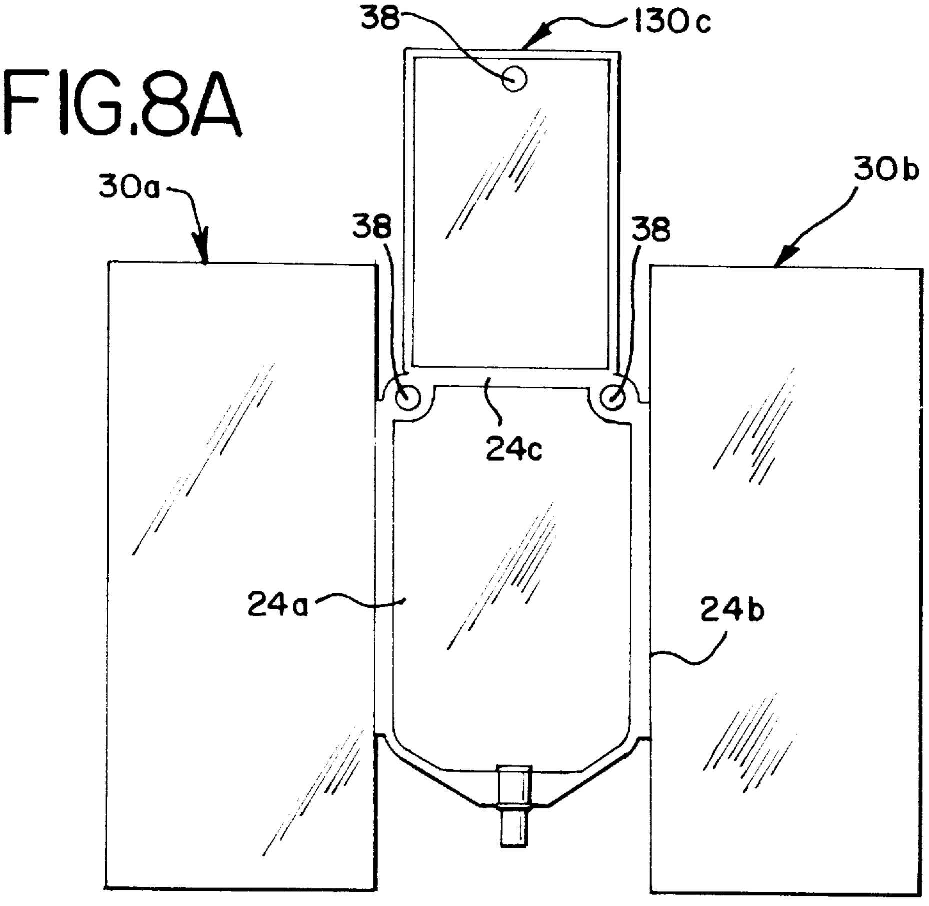
FIG. 8A is a front elevation view of a fourth embodiment of the container of the present invention having multiple flaps extending from adjacent sides of the container.

FIG. 8A displays an embodiment wherein an additional flap 130*c* extends from the top edge 24*c* of the chamber 22. Flap 130*c* is generally utilized to carry information. In this embodiment, the container 20 includes dual exterior apertures 38 on the body of the container 20. Dual exterior apertures 38 allows the container 20 to be held with hooks while still being able to rotate the flap 130*c* from the first surface 26 to the second surface 28. If rotation of flap 130*c* is not necessary, a single aperture 38 at the top of the flap 130*c* can be utilized.

Figure 9:
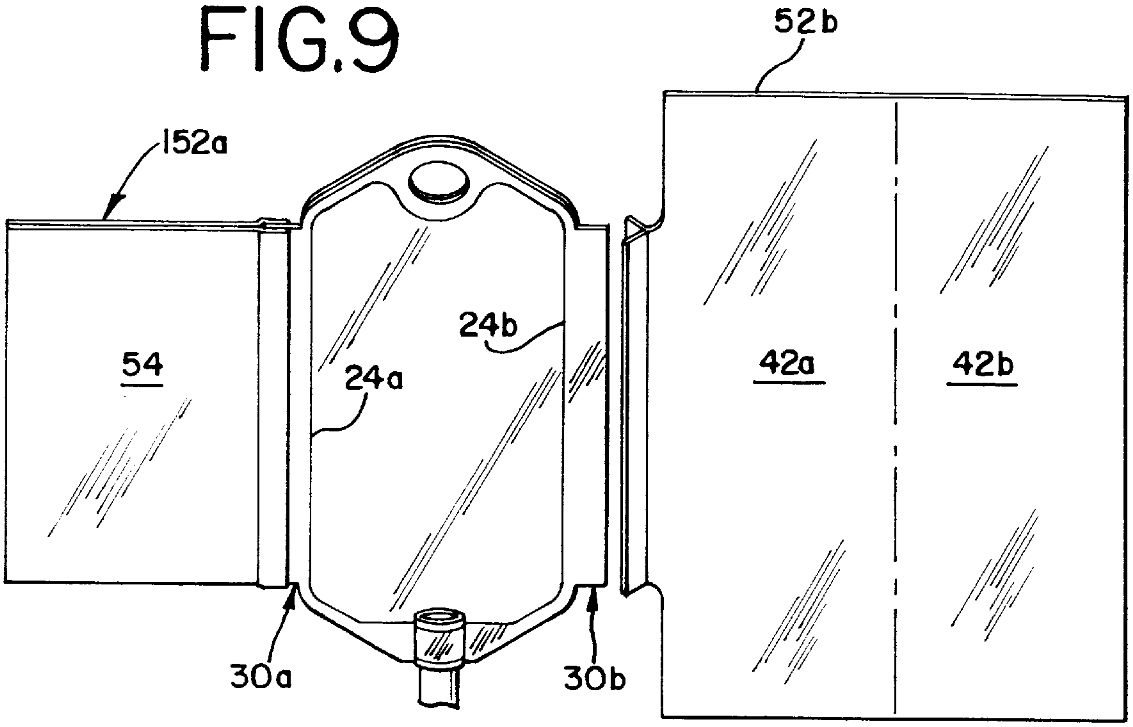
FIG. 9 is a front elevation view of a fifth embodiment of the container of the present invention having flaps and extensions.

Yet another embodiment is shown in FIG. 9. In this embodiment the protective coverings and information carriers are generally formed in two parts. First, narrower flaps 30*a*,30*b* extend from the chamber 22. The narrower flaps 30*a*,30*b* are similar in all respects to the standard flaps, except for the width dimension. Further, flaps 30*a*,30*b* are not only hingedly connected to the edges 24*a*,24*b* of the chamber 22, but they also serve as hinges themselves for extensions 152*a*,52*b*. Extensions 152*a*,52*b* connect to the flaps 30*a*,30*b* adjacent their respective peripheries 56*a*,56*b*. The extensions 152*a*,52*b* are connected to the flaps 30*a*,30*b* with any type of adhesive or welding technique, similar to those described herein. Additionally, an information carrying extension 152*a* can be formed from a label 54. As such, a label 54 having adhesive on one surface is folded over on itself so that the adhesive surface sticks partially together and partially to opposite sides of the flap 30*a* in overlapping relation, as shown in FIG. 9.

Figure 10:
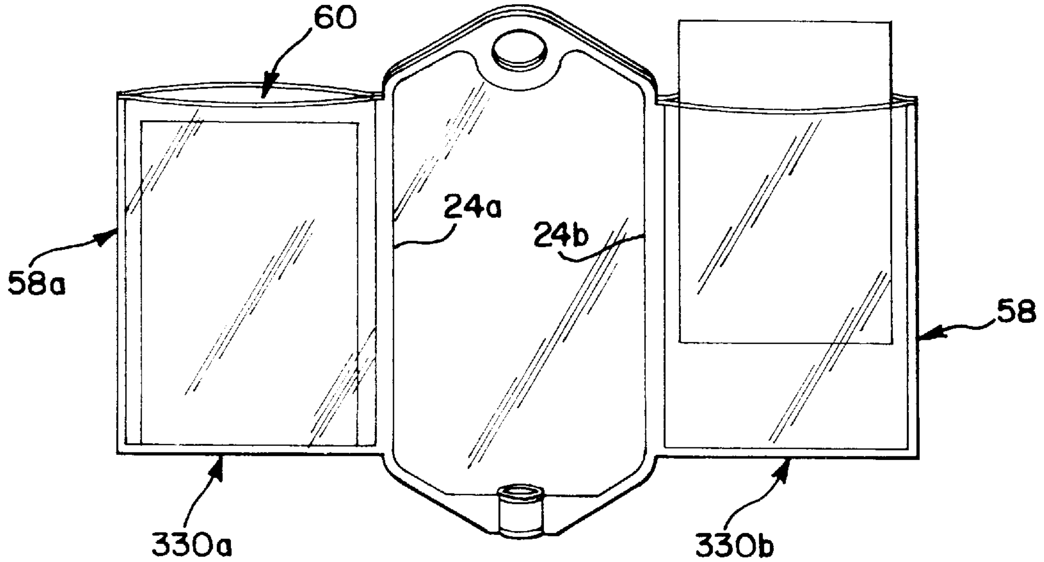
FIG. 10 is a front elevation view of the container of the present invention including pockets.

Referring now to FIG. 10, another embodiment of the present invention is illustrated. This embodiment has a special flap 330*a*,330*b* which is utilized to carry information. Flap 330*a*,330*b* has an opening 60 defining a pocket 58*a*,58*b*. The pocket 58*a*,58*b* is defined either by two superimposed pieces of material, or by a single piece of material which is overlapped and joined at edge 24*a*,24*b*. The materials or sheets forming the pocket 58*a*,58*b* are integrally formed with the materials of the first and second surfaces 26,28 of the container 20. Additionally, however, the pocket may be formed from an extension similar to that illustrated in FIG. 9, with the extension being connected to a periphery of a flap. The information is then inserted into the pockets 58*a*,58*b* and the openings 60 are sealed to retain the information. Alternatively, information may be reverse printed on an inside surface of the pocket 58*a*,58*b*. Multiple layers of information may be displayed simultaneously using reverse printing in combination with one or more of the previously described techniques. By placing the information inside the pockets 58*a*,58*b*, the information is protected from damage by abrasion and moisture.

In general, the container 20 may be made from virtually any weldable flexible plastic sheet material, extruded or coextruded material, or laminate material, such as polyvinyl chloride, polyolefins, polyethylene, polyethylene copolymers with comonomers selected from α-olefins having from 2–10 carbons, lower alkyl acrylates, vinyl acetate, vinyl alcohol and the like, and polyolefin blends. More preferably, the material is a polyolefin blend such as those polymer blends described in WO 95/14739 and the multi-layered structures set forth in U.S. Ser. No. 08/153,602 which are incorporated herein by reference and made a part hereof. Additionally, the material is transparent so the medical solution held in the chamber, and information placed in the pocket(s) or on the flaps, may be viewed without opening the container. The material typically has an optical haze level of less than 30% when measured according to ASTM D-1003. With this type of optical haze level, periodic visual inspection of medical solutions may be readily performed.

Figure 11:
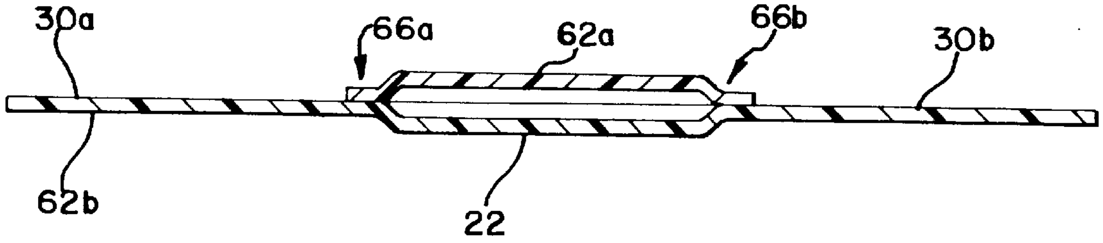
FIGS. 11, 11A and 11B are cross section views of the container of the present invention, displaying alternate constructions of the container.
Figure 11A:
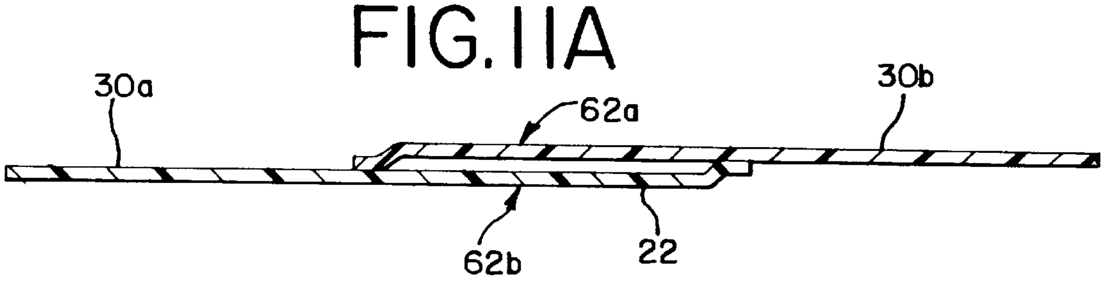
Figure 11B:
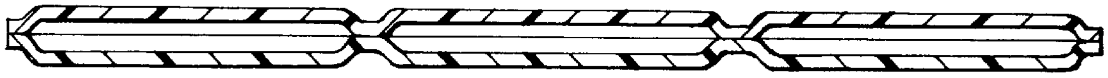

To manufacture the container 20, first and second pieces of weldable flexible plastic material 62*a*, 62*b*, respectively, are superimposed as shown in either FIGS. 2, 11 or 11A. In the container illustrated in FIG. 2, material 62*a* and material 62*b* entirely overlap each other. As such, each flap 30*a*,30*b* has a 2-ply thickness. In the container illustrated in FIG. 11, material 62*a* only overlaps material 62*b* enough to create the chamber 22. As such, material 62*b* forms both flaps 30*a* and 30*b*. Finally, in the container illustrated in FIG. 11A, each material 62*a*,62*b* forms a single flap 30*a* or 30*b*, and a single surface of the chamber 22. The material may be in sheet form. Once the materials 62*a*,62*b* are positioned, they are welded together using any of the above mentioned welding techniques.

Figure 12:
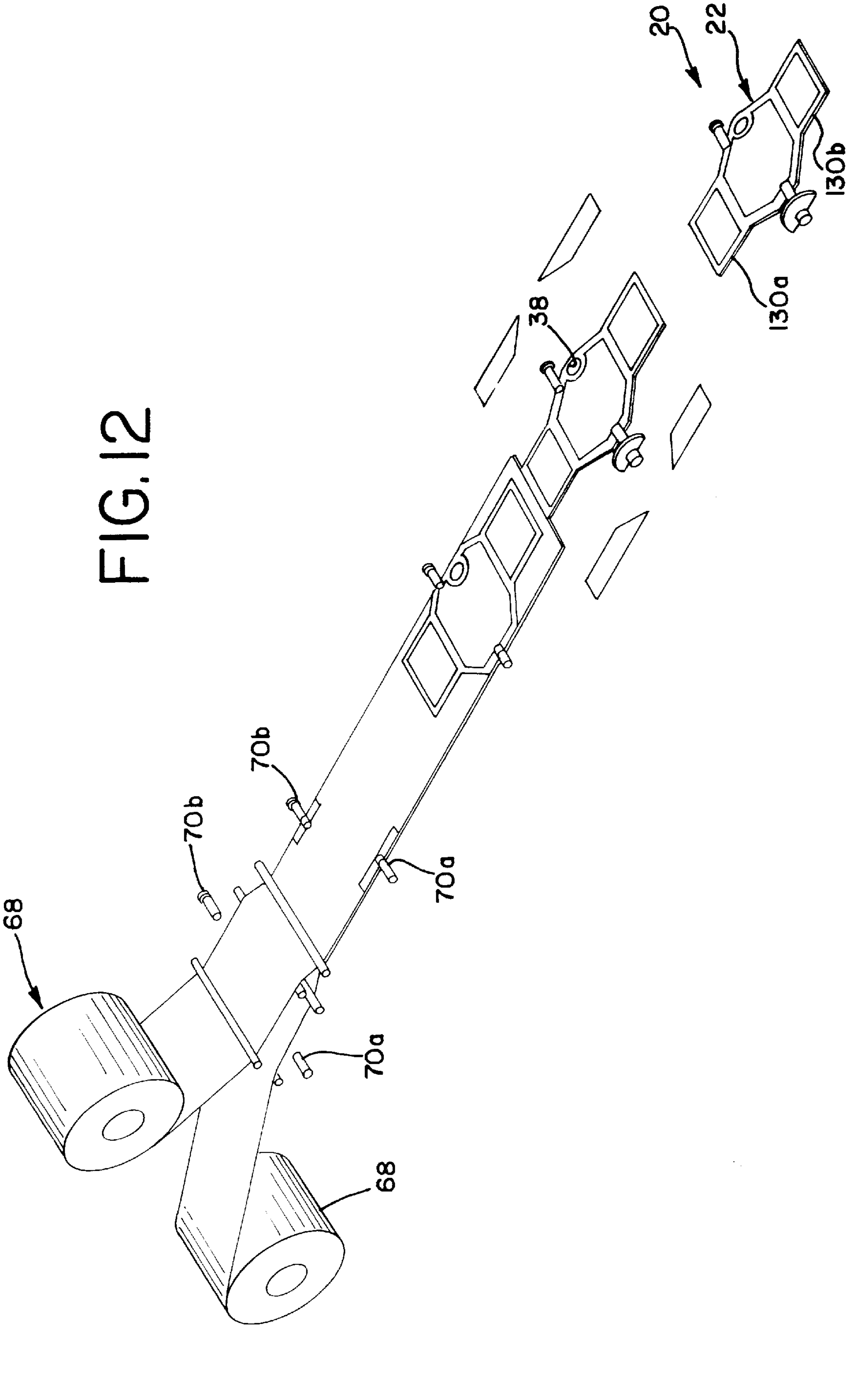
FIG. 12 is a schematic showing a sequence of steps for making a container of the present invention.

FIG. 12 further illustrates a method of making the container 20 of the present invention. Two webs of material are unwound from rolls 68 and superimposed with respect to one another. Port assemblies 70*a*, 70*b* are inserted between the webs at spaced intervals along opposite edges thereof before the webs pass through a sealing mechanism (not shown) which welds the port assemblies 70*a*,70*b* in place. The webs then pass through a second sealing and die mechanism (not shown) which welds the webs together to form the side, top and bottom seals 66*a*–66*d* of the chamber 22, along the peripheries of the flaps. The aperture 38 is also formed. Waste 72 is trimmed from the containers 20 after the webs pass through the second sealing mechanism. The containers 20 are then separated from the webs. Each completed container 20 is sterilized and filled via the port assembly 70*b* adjacent the aperture 38. Once the container 20 is filled, the chamber 22 is sealed adjacent the port assembly 70*b* and the port assembly 70*b* is trimmed from the container 20. When the container 20 is filled in this way, the other port assembly 70*a* is sealed prior to installation as part of the container 20. Alternately, the container 20 may be filled through the port assembly 70*a* positioned opposite the aperture 38, and the second port assembly 70*b* may be omitted entirely.

While specific embodiments have been illustrated and described, numerous modifications are possible without departing from the spirit of the invention, and the scope of protection is only limited by the scope of the accompanying claims.

We claim:

1. A container for holding medical solutions, the container comprising:

first and second pieces of sheet material forming a fluid-tight chamber, the chamber having opposing first and second edges and opposing first and second surfaces;

a first substantially flat charrberless flap comprising the first and second pieces of sheet material being attached together about adjacent surfaces, the flap extending from the first edge of the chamber and being hingedly connected to the chamber; and a second substantially flat chamberless flap extending from the second edge of the chamber and being hingedly connected to the chamber, wherein the first flap is positioned such that the first flap overlies the first surface of the chamber, and wherein the second flap is positioned such that the second flap overlies the second surface of the chamber.

2. The container of claim 1, wherein the first flap is sealably connected to the second flap proximate the periphery of the flaps, the chamber being encased between the first and second flaps.

3. The container of claim 1, wherein another flap extends from an edge of the chamber adjacent the first flap.

4. The container of claim 1, wherein the container is made from a sealable-flexible plastic material.

5. The container of claim 1, wherein the flap is made from a high vapor barrier material.

6. The container of claim 1, further comprising a sealable port in fluid communication with an interior of the chamber.

7. The container of claim 1, further comprising a sealable strip for sealing the container.

8. The container of claim 1, wherein the first flap is positioned such that the first flap at least partially overlies the first and second surfaces of the chamber.

9. The container of claim 1, wherein the container is made from a material having an optical haze level of less than 30% when measured according to ASTM D-1003.

10. A container for holding medical solutions, the container comprising:

first and second pieces of sheet material forming a fluid-tight chamber, the chamber having opposing first and second edges opposing first and second surfaces;

a substantially flat chamberless flat, extending from one of the edges of the chamber and being hingedly connected to the chamber wherein the substantially flat chamberless flap has a fold-line distal from the chamber, and wherein the flap is folded in an area proximate its fold-line such that the flap has a first and second section, the first and second sections having a periphery.

11. The container of claim 10, wherein the first section is positioned such that at least part of the first section overlies the first surface of the chamber, and the second section is positioned such that at least part of the second section overlies the second surface of the chamber.

12. The container of claim 11, wherein the first section of the flap is sealably connected to the second section of the flap proximate their peripheries, the chamber being encased between the first and second sections of the flap.

13. A container for holding medical solutions, the container comprising:

first and second pieces of sheet material forming a fluid-tight chamber, the chamber having opposing first and second edges and opposing first and second surfaces;

a substantially flat chamberless flap extending from one of the edges of the chamber and being hingedly connected to th chamber, wherein the flap comprises at least two superimposed materials joined along their respective peripheries at three edges thereof, to define a packet, with a fourth edge of the periphery of the at least two superimposed materials being substantially open forming a mouth of the pocket.

14. The container of claim 13, wherein the opening of the pocket is sealable for retaining information in the pocket.

15. A container for holding medical solutions, the container comprising:

first and second pieces of sheet material forming a fluid-tight chamber, the chamber having opposing first and second edges and opposing first and second surfaces;

a substantially flat chamberless flap extending from one of the edges if the chamber and being hingedly connected to the chamber, wherein the flap has peripheries, and wherein a label is connected to the flap adjacent at least one of the peripheries.

16. The container of claim 15, wherein the container is made from a scalable-flexible plastic material.

17. The container of claim 15, wherein the flaps are made from a high vapor barrier material.

18. A container for holding medical solutions, the container comprising:

at least first and second pieces of sheet material forming a fluid-tight chamber, the chamber having opposing first and second edges and opposing first and second surfaces;

a first flap comprising a portion of the first piece of sheet material extending from one of the first and second edges of the chamber, and a second flap comprising a portion of the second piece of sheet material extending from the same edge of the chamber as that of the first flap, the flaps being hingedly connected to the chamber, and the first and second flaps each having a periphery, wherein the first flap is positioned such that the first flap overlies the first surface of th chamber, and wherein the second flap is positioned such that the second flap overlies the second surface of the chamber.

19. The container of claim 18, wherein the first and second flaps are sealably connected to each other around the chamber such that the first and second flaps sealably encase the chamber.

20. The container of claim 18, wherein the container is made from a sealable-flexible plastic material.

21. The container of claim 18, wherein the container is made from a material having an optical haze level of less than 30% when measured according to ASTM D-1003.

22. A container for holding medical solutions, the container comprising:

a fluid-tight chamber, the chamber having opposing first and second edges and opposing first and second surfaces, the chamber comprising first and second pieces of sheet material being attached together about adjacent surfaces; and, a flap extending from an edge of the chamber, the flap being hingedly connected to the chamber, and the flap having a fold-line distal from the chamber, wherein the flap is folded in an area proximate its fold-line such that the flap has a first and second section, the first and second sections being substantially equal in size, such that the first section overlies the first surface of the chamber, and wherein the second section of the flap is positioned such that the second section overlies the second surface of the chamber.

23. The container of claim 22, wherein the first section of the flap is sealably connected to the second section of the flap substantially about the periphery thereof, the chamber being encased between the first and second sections of the flap.

24. The container of claim 22, wherein the container is made from a sealable-flexible plastic material.

25. The container of claim 22, further comprising a sealable strip for sealing the container.

26. The container of claim 22, wherein the container is made from a material having an optical haze level of less than 30% when measured according to ASTM D-1003.

* * * * *